United States Patent [19]

Chandraratna

[11] Patent Number: 4,810,804

[45] Date of Patent: Mar. 7, 1989

[54] ACETYLENES DISUBSTITUTED WITH A PHENYL GROUP AND A HETEROBICYCLIC GROUP HAVING RETINOID-LIKE ACTIVITY

[75] Inventor: Roshantha A. S. Chandraratna, El Toro, Calif.

[73] Assignee: Allergan, Inc., Irvine, Calif.

[21] Appl. No.: 31,476

[22] Filed: Mar. 26, 1987

[51] Int. Cl.⁴ .................. C07D 215/14; C07D 311/58; A61K 31/335; A61K 31/47

[52] U.S. Cl. ..................................... 514/311; 514/432; 514/456; 546/152; 549/23; 549/348; 549/407

[58] Field of Search ....................... 514/311, 432, 456; 546/152; 549/23, 398, 407

[56] References Cited

FOREIGN PATENT DOCUMENTS 2119801 11/1983 United Kingdom .................. 549/23

*Primary Examiner*—Mary C. Lee
*Assistant Examiner*—Mary Sue Howard

*Attorney, Agent, or Firm*—James M. Kanagy; Stuart A. Suter

[57] ABSTRACT

Retinoid-like activity is exhibited by compounds of the formula

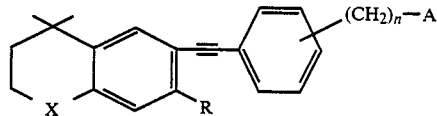

where X is S, O or $NR_1$ where $R_1$ is hydrogen or lower alkyl; n is 0-5; R is H or lower alkyl and A is H, —COOH or a pharmaceutically acceptable salt, ester or amide thereof, —$CH_2OH$ or an ether or ester derivative thereof, or —CHO or an acetal derivative thereof, or —$COR_2$ or a ketal derivative thereof where $R_2$ is —$(CH_2)_mCH_3$ where m is 0-4; or a pharmaceutically acceptable salt.

20 Claims, No Drawings

ACETYLENES DISUBSTITUTED WITH A PHENYL GROUP AND A HETEROBICYCLIC GROUP HAVING RETINOID-LIKE ACTIVITY

BACKGROUND

This invention relates to novel compounds having retinoid-like activity. More specifically, the invention relates to compounds having a substituted ethynylphenyl function and a second portion which is a tetrahydroquinolinyl, thiochromanyl, or chromanyl group. It is anticipated that the oxidation products of these compounds, particularly the oxides of the thiochromanyl compounds, will have activity similar to that of their parent compound.

RELATED ART

Carboxylic acid derivatives useful for inhibiting the degeneration of cartilage of the general formula 4-(2-(4,4-dimethyl-6-X)-2-methylvinyl)benzoic acid where X is tetrahydroquinolinyl, chromanyl or thiochromanyl are disclosed in European patent application No. 0133795 published Jan. 9, 1985. See also European patent application No. 176034A published Apr. 2, 1986 where tetrahydronaphthalene compounds having an ethynylbenzoic acid group are disclosed.

SUMMARY OF THE INVENTION

This invention covers compounds of formula I

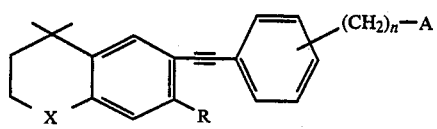

where X is S, O or $NR_1$ where $R_1$ is hydrogen or lower alkyl; n is 0–5; R is H or lower alkyl and A is H, —COOH or a pharmaceutically acceptable salt, ester or amide thereof, —CH$_2$OH or an ether or ester derivative thereof, or —CHO or an acetal derivative thereof, or —COR$_2$ or a ketal derivative thereof where $R_2$ is —(CH$_2$)$_m$CH$_3$ where m is 0–4; or a pharmaceutically acceptable salt.

In a second aspect, this invention relates to the use of the compounds of formula I for treating dermatoses, such as acne, Darier's disease, psoriasis, icthyosis, eczema, atopic dermatitis and epithelial cancers. These compounds are also useful in the treatment of arthritic diseases and other immunological disorders (e.g., lupus erythematosus), in promoting wound healing for treating the dry eye syndrome and in reversing the effects of sun damage on skin.

This invention also relates to a pharmaceutical formulation comprising a compound of formula I in admixture with a pharmaceutically acceptable excipient.

In another aspect, this invention relates to the process for making a compound of formula I which process comprises reacting a compound of formula II with a compound of formula III in the presence of Pd(PQ$_3$)$_4$ (Q is phenyl) or a similar complex

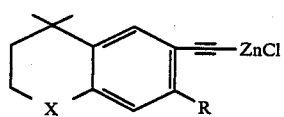

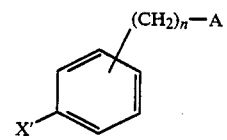

where X' is a halogen, preferably I; R is hydrogen or lower alkyl, n is the same as defined above; and A is H, or a protected acid, alcohol, aldehyde or ketone giving a compound of formula I; or homologating a compound of the formula

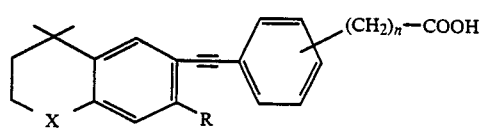

where n is 0–4 to give an acid compound of formula I; or
converting an acid of formula I to an acid salt; or
converting an acid of formula I to an ester; or
converting an acid of formula I to an amide; or
reducing an acid of formula I to an alcohol or aldehyde; or
converting an alcohol of formula I to an ether or ester; or
oxidizing an alcohol of formula I to an aldehyde or ketone; or
converting an aldehyde of formula I to an acetal; or
converting a ketone of formula I to a ketal.

GENERAL EMBODIMENTS

Definitions

The term "ester" as used here refers to and covers any compound falling within the definition of that term as classically used in organic chemistry. Where A is —COOH, this term covers the products derived from treatment of this function with alcohols. Where the ester is derived from compounds where A is —CH$_2$OH, this term covers compounds of the formula —CH$_2$OOCR where R is any substituted or unsubstituted aliphatic, aromatic or aliphatic-aromatic group.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Here, and wherever else used, lower alkyl means having 1-6 carbon atoms. Also preferred are the phenyl or lower alkylphenyl esters.

Amides has the meaning classically accorded that term in organic chemistry. In this instance it includes the unsubstituted amides and all aliphatic and aromatic mono- and di-substituted amides. Preferred amides are the mono- and di-substituted amides derived from lower alkyl substituted amines or the lower alkyl aliphatic cyclic or aromatic (phenyl for example) substituted amines. Particularly preferred amides are those derived from mono- or di-lower alkyl substuted amines. Also preferred are mono- and di-substituted amides derived from the phenyl or lower alkylphenyl amines. Unsubstituted amides are also preferred.

Acetals and ketals include the radicals of —CK where K is (—OR)$_2$. Here, R is lower alkyl. Also, K may be —OR₁ O— where $R_1$ is lower alkyl of 2–5 carbon atoms, straight chain or branched.

A pharmaceutically acceptable salt may be prepared for any compound in this disclosure having a functionality capable of forming such salt, for example an acid or an amine functionality. A pharmaceutically acceptable salt is any salt which retains the activity of the parent compound and does not impart any deleterious or untoward effect on the subject to which it is administered and in the context in which it is administered.

A pharmaceutically acceptable salt of an acid may be derived from an organic or inorganic base. Such salt may be a mono- or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where acid addition salts are formed from amines, any inorganic or organic acid may be used. Preferred salts are hydrogen chloride salts, sulfate salts, phosphate salts and salts of simple organic acids of 2 to 6 carbons, either the mono- or diacids. Quarternary ammonium compounds can be prepared from alkylating agents such as methyl iodide and the like.

The preferred compounds of this invention are those where the radical designated $(CH_2)_n$—A is para to the ethynyl group on the phenyl ring; n is 0, 1 or 2; and A is —COOH or an alkali metal salt or organic amine salt thereof or a lower alkyl ester, or —CH₂OH and the lower alkyl esters and ethers thereof. The more preferred compounds are:

4-[4,4-dimethylthiochroman-6-ylethynyl]benzoic acid;
ethyl 4-[4,4-dimethylthiochroman-6-ylethynyl]benzoate;
ethyl 4-[4,4-dimethylchroman-6-ylethynyl]benzoate; and
4-[4,4-dimethylchroman-6-ylethynyl)]benzoic acid.

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne, oral administration may also be used. Any common topical formulation such as a solution, suspension, gel, ointment, or salve and the like may be used. Preparation of such topical formulations are well described in the art of pharmaceutical formulations as exemplified, for example, *Remington's Pharmaceutical Science*, Edition 17, Mack Publishing Company, Easton, Pa. For topical application, these compounds could also be administered as a powder or spray, particularly in aerosol form.

If the drug is to be administered systemically, it may be confected as a powder, pill, tablet or the like, or as a syrup or elixir for oral administration. For intravenous or intraperitoneal administration, the compound will be prepared as a solution or suspension capable of being administered by injection. In certain cases, it may be useful to formulate these compounds in suppository form or as an extended release formulation for deposit under the skin or intramuscular injection.

Other medicaments can be added to such topical formulation for such secondary purposes as treating skin dryness, providing protection against light; other medications for treating dermatoses, preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation. However, it is anticipated that in the treatment of, for example, acne, or other such dermatoses, that a formulation containing between 0.001 and 5 percent by weight, preferably about 0.01 to 1%, will usually constitute a therapeutically effective concentration. If administered systemically, an amount between 0.01 and 100 mg per kg body weight per day, but preferably about 0.1 to 10 mg/kg, will effect a therapeutic result in most instances.

The retinoic acid like activity of these compounds was confirmed through the classic measure of retinoic acid activity involving the effects of that compound on ornithine decarboxylase. The original work on the correlation between retinoic acid and decrease in cell proliferation was done by Verma & Boutwell, *Cancer Research*, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increase are unknown, it is known that 12-O-tetradecanoylphorbol-13-acetate (TPA) induces ODC activity. Retinoic acid inhibits this induction of ODC activity by TPA. The compounds of this invention also inhibit TPA induction of ODC as demonstrated by an assay essentially following the procedure set out in *Cancer Res.*: 1662–1670, 1975.

SPECIFIC EMBODIMENTS

The compounds of this invention can be made by a number of different synthetic chemical pathways. To illustrate this invention, there is here outlined a series of steps used to make the compounds of formula I when such synthesis is followed in tone and in spirit. The synthetic chemist will readily appreciate that the conditions set out here are specific embodiments which can be generalized to any and all of the compounds represented by formula I.

Compounds of formula I where X is sulfur are prepared as per Reaction Scheme I.

Reaction Scheme I

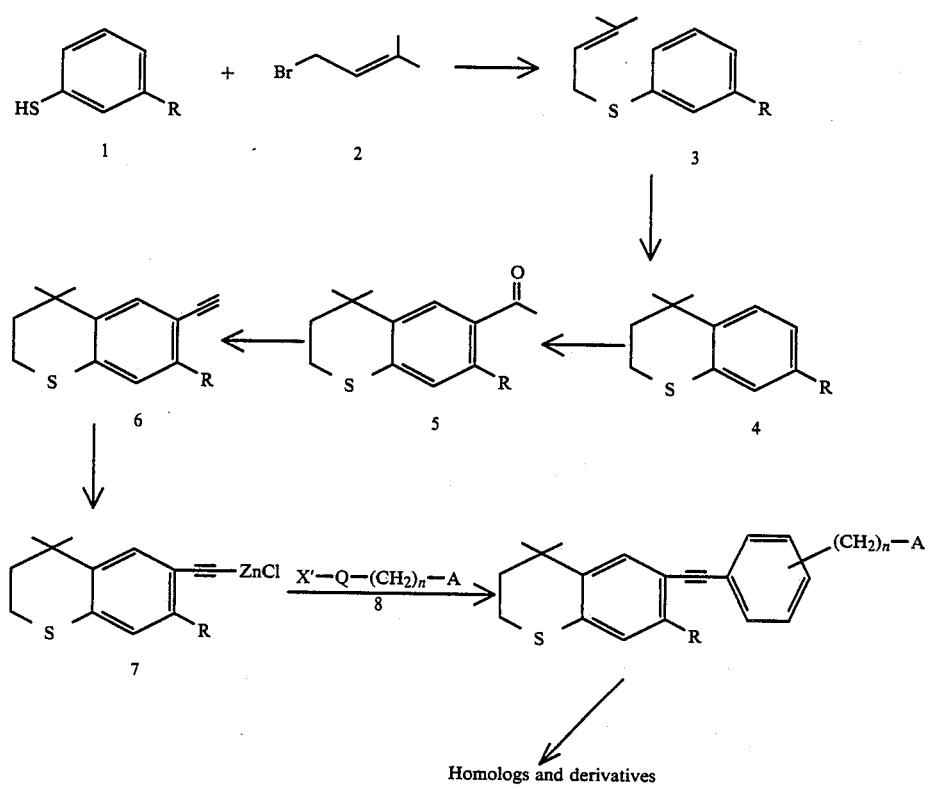

Homologs and derivatives

Here, n is 0-5, R is hydrogen or lower alkyl, A is H, or a protected acid, alcohol, aldehyde or ketone and Q is phenyl. X' may be Br, Cl or I, but Br and I are prefered when n is O and is I when n is 1-5.

Generalized reaction conditions applicable to the synthesis described in Reaction Scheme I are described below. The thiophenol of formula 1 is first treated with an approximately equimolar amount of a strong base such as an alkali metal hydroxide, preferably sodium hydroxide, in a polar solvent such as acetone at reflux for between 1 and 4 hours, preferrably 2.5 hours, after which the solution is treated with an equimolar amount of formula 2, 1-bromo-3-methyl-2-butene (Aldrich), and dissolved in the solvent. Then, refluxing is continued for about 2 days after which the solution is stirred for another 24 hours at about room temperature effecting formation of formula 3. Product is isolated by conventional means.

Ring closure is effected (compound 4) by treating the sulfide, whose formation is described above, with phosphorous pentoxide in the presence of phosphoric acid under an inert atmosphere. The sulfide is first dissolved in an inert solvent such as benzene, toluene, or the like, and then treated with a small excess of phosphorous pentoxide along with concentrated phosphoric acid. The solution is heated at reflux with stirring under an inert gas such as argon or nitrogen for up to 24 hours. The product is then recovered and purified by conventional means.

The ketone of formula 5 is obtained by treating the thiochroman compound with acetyl chloride in the presence of aluminum chloride. A suspension of the aluminum chloride in a polar inert solvent is prepared under an inert atmosphere and at reduced temperature, i.e., −10° to 10° C. The inert atmosphere may be argon or nitrogen, preferably argon. The reaction is conveniently carried out in a solvent such as methylene chloride. To the aluminum chloride suspension is added the thiochroman and acetyl chloride via a dropping funnel or similar device. About a 5% molar excess of acetyl chloride and 10% molar excess of aluminum chloride, relative to the thiochroman material, is used. The reaction is effected with agitation (stirring) over 0.5-4 hours at a temperature between 10°-50° C. Preferably the reaction is effected in about 2 hours at room temperature. Then the reaction is quenched with water and/or ice, the product extracted and further purified by distillation or some other appropriate means.

The acetylenic function on formula 6 is introduced by means of lithium diisopropylamide, or a similar base, at reduced temperature under an inert atmosphere. The reaction is carried out in an ether-type of solvent such as a dialkyl ether or a cyclic ether, for example, tetrahydrofuran, pyran or the like.

More specifically, lithium diisopropylamide is generated in situ by mixing diisopropylamine in a dry solvent such as tetrahydrofuran, which is then cooled, to between −70° and −50° C. under an inert atmosphere. An equimolar amount of an alkyllithium compound such as n-butyl lithium in an appropriate solvent is then added at the reduced temperature and mixed for an appropriate time to permit formation of lithium diisopropylamide (LDA). The ketone of formula 5 (at least a 10% molar excess) is dissolved in the reaction solvent, the solution cooled to that of the LDA mixture, and added to that solution. After brief mixing, the solution is then treated with a dialkyl chlorophosphate, preferably diethyl chlorophosphate in about a 20% molar excess. The reaction solution is then gradually brought to room temperature. This solution is then added to a second lithium diisopropylamide solution which is prepared in situ using dry solvent and under an inert atmosphere, preferrably argon, at reduced temperature (eg. −78° C.). Then the reaction mixture is again warmed to room temperature where it is stirred for an extended period of time, preferably between 10 and 20 hours, most preferably about 15 hours. The solution is then acidified and the product recovered by conventional means.

Formula 7 compounds, the zinc chloride salts, are prepared under conditions which exclude water and oxygen. A dry, ether-type solvent such as dialkyl ether or a cyclic ether such as a furan or pyran, particularly a tetrahydrofuran, may be used as the solvent. A solution of formula 6 is first prepared under an inert atmosphere such as argon or nitrogen, and then a strong base such as n-butyl lithium is added (in about a 10% molar excess). This reaction is begun at a reduced temperature of between −10° and +10° C., preferably about 0° C. The reaction mixture is stirred for a short period, between 30 minutes and 2 hours, and then treated with about a 10% molar excess of fused zinc chloride dissolved in the reaction solvent. This mixture is stirred for an additional 1–3 hours at about the starting temperature, then the temperature is increased to about ambient temperature for 10–40 minutes.

Compounds of Formula I are prepared by coupling the ZnCl salts of formula 7 with the halogen substituted phenyl-based fragment of formula 8 where A is hydrogen or a protected acid, alcohol, aldehyde or ketone or hydrogen. These latter compounds, the protected acid, etc., are all available from chemical manufacturers or can be prepared by published methods. If the starting material is an acid, it is esterified by refluxing the acid in a solution of the appropriate alcohol in the presence of thionyl chloride. Refluxing for 2–5 hours provides the desired ester. The ester is recovered and purified by conventional means. Alcohols, aldehydes and ketones all may be protected by forming respectively, ethers and esters, acetals or ketals by known methods such as those described in *McOmie*, Plenum Publishing Press, 1973 and *Protecting Groups*, Ed. Greene, John Wiley & Sons, 1981.

To increase the value of n, where such compounds are not available from a commercial source, the halogen substituted benzoic acid or phenylalkyl acid homlogues are subjected to homologation by successive treatment under Arndt-Eistert conditions. These acids are then esterified by the general procedure outlined in the preceeding paragraph. Also, from such acids can be prepared the corresponding alcohol or aldehyde, which, after esterification or the formation of an acetal, or similar protecting reaction, is used in the coupling reaction following.

To make formula I, (via a coupling reaction) formula 8 is first dissolved in a dry reaction solvent. The formula 8 compound is used in an amount approximating the molar concentration of formula 7. This solution is introduced into a suspension of tetrakis-triphenylphosphine palladium (about a 5 to 10% molar amount relative to the reactants) in the reaction solvent at a temperature of between about −10° and +10° C. This mixture is stirred briefly, for about 15 minutes. To this just prepared mixture is then added the pre-prepared solution of formula 7, the addition being made at about room temperature. This solution is stirred for an extended period, between about 15 and 25 hours at room temperature. The reaction is then quenched with acid and the product separated and purified by conventional means to give the compounds of formula I.

An alternative means for making compounds where n is 1–5 is to subject the compounds of formula I where n=0 and A is an acid function to homologation using the Arndt-Eistert method referred to above.

Compounds of formula I where X is oxygen are prepared as per Reaction Scheme II.

Reaction Scheme II

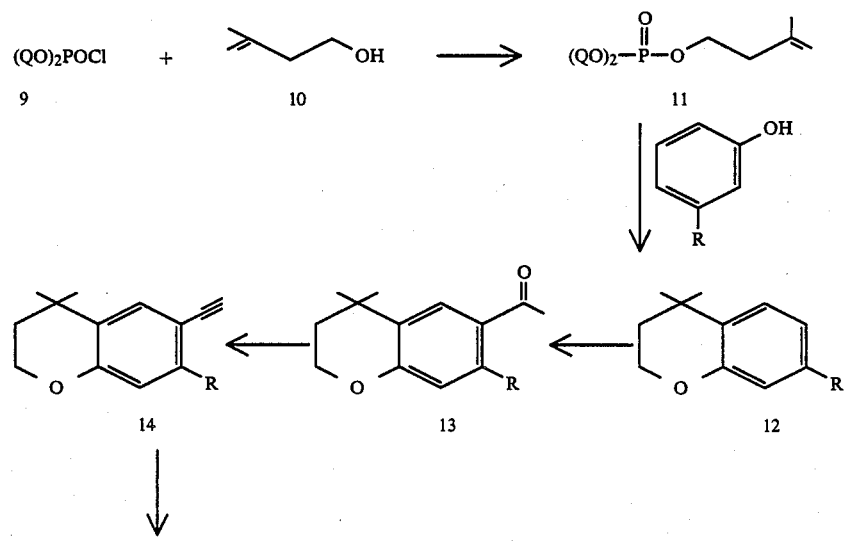

-continued
Reaction Scheme II

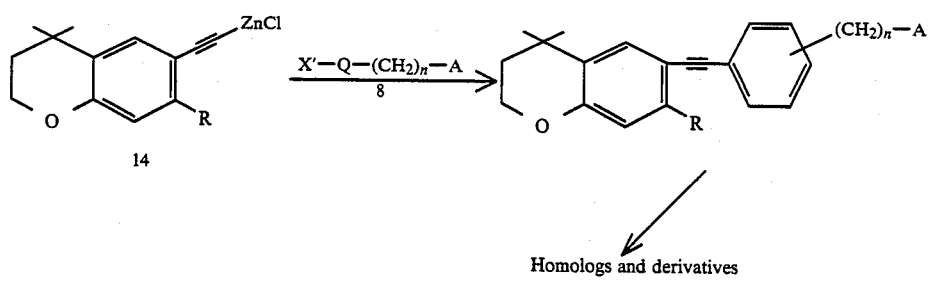

Here, as in Reaction Scheme I, n is 0-5, R is hydrogen or lower alkyl, A is H, or a protected acid, alcohol, aldehyde or ketone and X' may be Br, Cl or I, but Br and I are preferred when n is 0 and is I when n is 1-5.

These compounds are prepared as follows. The phosphate of formula 11 is prepared from the corresponding diphenyl chlorophosphate and 3-methyl-3-butene-1-ol available from Aldrich or prepared by means known in the art. It is preferred to prepare formula 11 by dissolving the alcohol of formula 10 in about a 10% excess of pyridine or the like under an inert atmosphere cooled to approximately $-10°$ to $10°$ C. This solution is then added drop-wise, under an inert atmosphere, to a solution of diphenyl chlorophosphate in about an equal amount of the reaction solvent. About a 2-5% molar excess of diphenyl chlorophosphate relative to the alcohol is employed. The atmosphere may be argon, nitrogen, or another inert gas. The mixture is heated at reflux for between 1 and 5 hours, preferably about 3, to effect the reaction. The product is then recovered by conventional means.

The diphenyl phosphate ester from the preceeding paragraph (formula 11) is then reacted with a phenol to effect formation of compound 12. For example, phenol is added to a flask already containing stannic chloride under argon which has been cooled to between $-10°$ to $10°$ C. After thorough mixing of this combination for about 15 minutes to an hour at the reduced temperature, the phosphate is added at the reduced temperature. Both of these steps are carried out under an inert atmosphere such as argon or nitrogen. When the addition of the phosphate is completed, the mixture is stirred at about ambient temperature for up to 24 hours. Then the reaction is quenched with a dilute solution of aqueous alkali metal base or the like. The product is recovered by extraction and other conventional means.

Thereafter, compounds of formula 12 are treated sequentially in the same manner as described for making the ketone, acetylenic compound and its ZnCl salts, the coupling reaction and then formation of Formula I compounds by the subsequent steps in Reaction Scheme I.

Where X is nitrogen, such compounds may be prepared by the following reaction scheme:

Reaction Scheme III

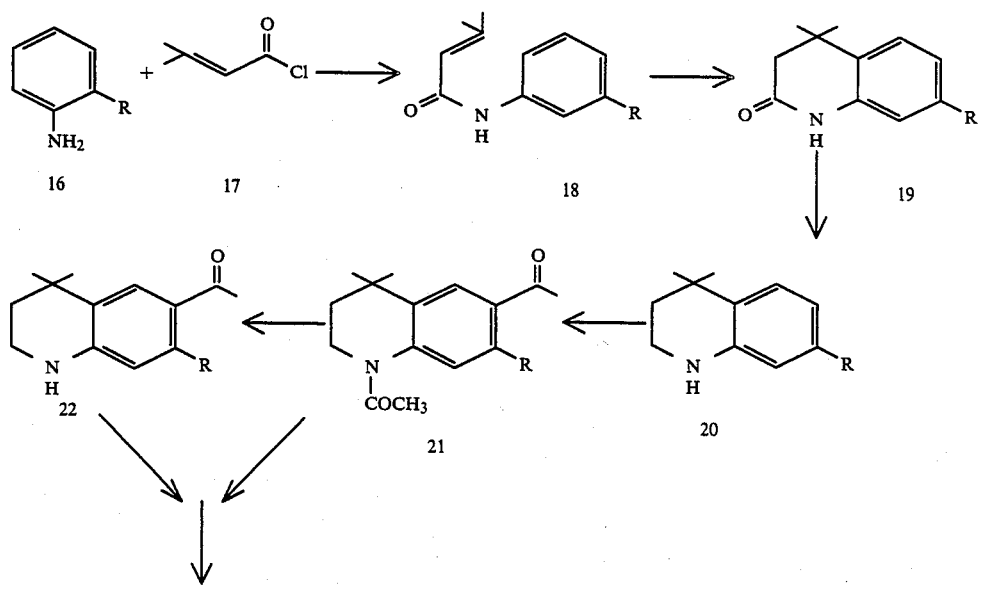

-continued
Reaction Scheme III

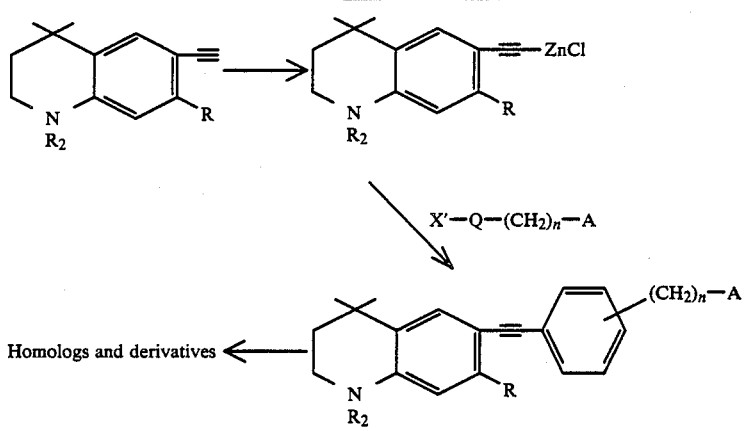

Here, as above, n is 0–5, A is H, or a protected acid, alcohol, aldehyde or ketone. $R_2$ may be hydrogen or a protecting group such as —$COCH_3$. X may be Br, Cl or I, but Br and I are prefered when n is 0 and is I when n is 1–5.

The tetrahydroquinoline moiety, that is where X is nitrogen, is made in part by the method described in European patent application No. 0130795 published Sept. 1, 1985. First, 3-methylcrotonoyl chloride is reacted with aniline to obtain the amide (formula 18). This amide is then cyclized using aluminum chloride in the absence of solvent to give formula 19. Lithium aluminum hydride or another acceptable reducing agent of similar type is then used to reduce the 2-oxo-1,2,3,4-tetrahydroquinoline, preferably in an inert solvent such a diethyl ether. This amine is then acetylated using acetyl chloride in a polar solvent such as pyridine followed by acetylation in the presence of aluminum chloride to give the compound of formula 21. The compound of formula 21 is then subjected to base hydrolysis to give the secondary amine of formula 22. The compound of formula 22 is treated as described in Reaction Scheme I for the preparation of compounds 6 and 7 to make compounds of formula 23 and 24, respectively. Compound of formula 25 is coupled as described before to give compounds of formula I.

The acids and salts derived from formula I are readily obtainable from the corresponding esters. Basic saponification with an alkali metal base will provide the acid. For example, an ester of formula I may be dissolved in a polar solvent such as an alkanol, preferably under an inert atmosphere at room temperature, with about a three molar excess of base, for example, potassium hydroxide. The solution is stirred for an extended period of time, between 15 and 20 hours, cooled, acidified and the hydrolysate recovered by conventional means.

The amide may be formed by any appropriate amidation means known in the art. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about —10° and +10° C. The last mentioned solution is then stirred at the reduced temperature for 1–4 hours, preferably 2 hours. Solvent removal provides a residue which is taken up in an inert inorganic solvent such as benzene, cooled to about 0° C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride (J. March, "Advanced Organic Chemistry", 2nd Edition, McGraw-Hill Book Company), and then reducing the acid chloride with sodium borohydride (March, Ibid, pg. 1124) which gives the corresponding alcohols; or by reducing th corresponding ester with lithium aluminium hydride at low temperatures. Alkylating these alcohols with appropriate alkyl halides under Williamson reaction conditions (March, Ibid, pg. 357) gives the corresponding ethers. Esters of these alcohols can be prepared by reacting the alcohols with carboxylic acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., Tet. Lett., 399, 1979) or dimethyl sulfoxide and oxalyl chloride in methylene chloride (Omura, K. Swen, D. Tetrahedron, 1978, 34, 1651).

Acetals and ketals can be prepared from the corresponding aldehyde or ketone by the method described in March, Ibid, p 810.

The following examples are set out to illustrate this invention, not to limit it.

EXAMPLE 1

Phenyl-3-methylbut-2-enylsulfide

A mixture of 14.91 g (135.324 mmol) of thiophenol and 5.5 g (137.5 mmol) of NaOH in 100 ml acetone was heated at reflux for 2.5 hours and then treated dropwise with a solution of 20 g (134.19 mmol) of 1-bromo-3-methyl-2-butene in 20 ml acetone. This solution was refluxed for 40 hours and then stirred at room temperature for 24 hours. Solvent was then removed in vacuo and the residue was taken up in water and extracted with 3×50 ml ether. Ether extracts were combined and washed with 3×30 ml of 5% NaOH solution, then water, saturated NaCl solution and dried ($MgSO_4$). Solvent was then removed in vacuo and the residue further purified by Kugelrohr distillation (80° C., 0.75 mm) to give the title compound as a pale yellow oil. PMR (CDCl) : δ1.57 (3H, s), 1.69 (3H, s), 3.52 (2H, d, J~7.7 Hz), 5.29 (1H, t, J~7.7 Hz), 7.14 (1H, t, J~7.0 Hz), 7.24 (2H, t, J~7.0 Hz), 7.32 (2H, d, J~7.0 Hz).

Proceeding in a similar manner, but substituting for thiophenol the appropriate 3-alkylthiophenol, the following compounds can be prepared:
3-methylphenyl-3-methylbut-2-enylsulfide;
3-ethylphenyl-3-methylbut-2-enylsulfide;
3-propylphenyl-3-methylbut-2-enylsulfide;
3-butylphenyl-3-methylbut-2-enylsulfide;
3-pentylphenyl-3-methylbut-2-enylsulfide; and
3-hexylphenyl-3-methylbut-2-enylsulfide.

EXAMPLE 2

4,4-Dimethythiochroman

To a solution of 15.48 g (86.824 mmol) of phenyl-3-methylbut-2-enylsulfide (from Example 1) in 160 ml benzene were added successively 12.6 g (88.767 mmol) of phosphorus pentoxide and 11 ml of 85% phosphoric acid. This solution was refluxed with vigorous stirring under argon for 20 hours, then cooled to room temperature. The supernatant organic layer was decanted and the syrupy residue extracted with 3×50 ml ether. Organic fractions were combined and washed with water, saturated NaHCO$_3$ and saturated NaCl solutions and then dried (MgSO$_4$). Solvent was removed in vacuo and the residue purified by kugelrohr distillation (80° C., 0.5 mm) to give the title compound as a pale yellow oil. PMR (CDCl$_3$) : δ 1.30 (6H, s), 1.90-1.95 (2H, m), 2.95-3.00 (2H, m), 6.96-7.00 (2H, m), 7.04-7.07 (1H, m), 7.30-7.33 (1H, m).

This method can be used to make 6-position alkyl analogues as exemplified by the following compounds:
4,4,7-trimethylthiochroman;
4,4-dimethyl-7-ethylthiochroman;
4,4-dimethyl-7-propylthiochroman;
4,4-dimethyl-7-butylthiochroman; and
4,4-dimethyl-7-hexylthiochroman.

EXAMPLE 3

4,4-Dimethyl-6-acetylthiochroman

A solution of 14.3 g (80.21 mmol) of 4,4-dimethylthiochroman (from Example 2) and 6.76 g (86.12 mmol) of acetyl chloride in 65 ml benzene was cooled in an ice bath and treated dropwise with 26.712 g (102.54 mmol) of stannic chloride. The mixture was stirred at room temperature for 12 hours, then treated with 65 ml water and 33 ml conc. hydrogen chloride and heated at reflux for 0.5 hours. After being cooled to room temperature, the organic layer was separated and the aqueous layer extracted with 5×50 ml benzene. The recovered organic fractions were combined and washed with 5% sodium carbonate, water, saturated NaCl and then dried (MgSO$_4$). The solvent was removed in vacuo and the residue purified by flash chromatography (silica; 5% ethyl acetate in hexanes) followed by kugelrohr distillation (150° C., 0.7 mm) to give the title compound as a pale yellow oil. PMR (CDCl): δ 1.35 (6H, s), 1.92-1.98 (2H, m) 2.54 (3H, s), 3.02-3.08 (2H, m), 7.13 (1H, d, J~8.6 Hz), 7.58 (1H, dd, J~8.6 Hz, 2 Hz), 7.99 (1H, d, J~2 Hz).

This procedure serves to acetylate all the compounds which can be made by the process in Example 2.

EXAMPLE 4

4,4-Dimethyl-6-ethynylthiochroman

To a solution of 1.441 g (14.2405 mmol) of diisopropylamine in 30 ml dry tetrahydrofuran under argon at −78° C. was added dropwise 9 ml of 1.6M (14.4 mmol) n-butyl lithium in hexane. After stirring this solution at −78° C. for 1 hour, it was treated dropwise with a solution of 2.95 g (13.389 mmol) of 4,4-dimethyl-6-acetylthiochroman (from Example 3) in 5 ml of dry tetrahydrofuran. After another hour of stirring at −78° C., the solution was treated with 2.507 g (14.53 mmol) of diethyl chlorophosphate and brought to room temperature, where it was stirred for 3.75 hours. This solution was then transferred using a double ended needle to a solution of lithium diisopropylamide [prepared using 2.882 g (28.481 mmol) of diisopropylamine and 18 ml of 1.6M (28.8 mmol) n-butyllithium in hexane] in 60 ml dry tetrahydrofuran at −78° C. The cooling bath was removed and the solution stirred at room temperature for 15 hours, then quenched with water and acidified to pH 1 with 3N hydrogen chloride. The mixture was extracted with 5×50 ml pentane and the combined organic fractions washed with 3N hydrogen chloride, water, saturated NaHCO$_3$ and saturated NaCl, then dried (MgSO$_4$). Solvent was then removed in vacuo and the residue purified by kugelrohr distillation (100° C., 0.7 mm) to give the title compound as a pale yellow solid. PMR (CDCl$_3$): δ 1.34 (6H,s), 1.94-1.99 (2H, m), 3.04-3.08 (3H, m), 7.06 (1H, d, J~8.4 Hz), 7.17 (1H, dd, J~8.4 Hz, 2.1 Hz), 7.51 (1H, d, J~2.1 Hz).

Similarly, the acetyl group of all compounds prepared as per Example 3 can be converted to an ethynyl function.

EXAMPLE 5

Ethyl 4-iodobenzoate

To a suspension of 10 g (40.32 mmol) of 4-iodobenzoic acid in 100 ml absolute ethanol was added 2 ml thionyl chloride and the mixture was then heated at reflux for 3 hours. Solvent was removed in vacuo and the residue was dissolved in 100 ml ether. The ether solution was washed with saturated NaHCO$_3$ and saturated NaCl solutions and dried (MgSO$_4$). Solvent was then removed in vacuo and the residue kugelrohr distilled (100° C.; 0.55 mm) to give the title compound as a colorless oil. PMR (CDCl$_3$): δ 1.42 (3H, t, J~7 Hz), 4.4 (2H, q, J~7 Hz), 7.8 (4H), In the same manner, but substituting for 4-iodobenzoic acid the appropriate acid, the following compounds can be prepared:
ethyl 4-iodophenylacetate;
ethyl 3-(4-iodophenyl)propionate;
ethyl 4-(4-iodophenyl)butanoate; and
ethyl 5-(4-iodophenyl)pentanoate.

EXAMPLE 6

Ethyl 4-[4,4-dimethylthiochroman-6-yl-ethynyl]benzoate

Reaction vessels used in this procedure were flame dried under vacuum and all operations carried out in an oxygen-free, argon or nitrogen atmosphere. To a solution of 533.9 mg (2.6389 mmol) of 4,4-dimethyl-6-ethynylthiochroman (from Example 4) in 4 ml of dry tetrahydrofuran at 0° C. was added dropwise 1.7 ml of 1.6M (2.72 mmol) n-butyl lithium in hexane. This was stirred at 0° C. for 10 minutes and at room temperature for 15 minutes, cooled again to 0° C. and then treated with a solution of 410 mg (3.005 mmol) of fused ZnCl₂ in 4 ml dry tetrahydrofuran using a double ended needle. Thereafter, the solution was stirred at 0° C. for 45 minutes, then at room temperature for 20 minutes. A solution of 724.4 mg (2.6243 mmol) of ethyl 4-iodobenzoate (from Example 5) in 4 ml dry tetrahydrofuran was transferred by double ended needle into a suspension of 520 mg (0.45 mmol) of tetrakistriphenylphosphine palladium in 5 ml dry tetrahydrofuran and stirred at room temperature for 20 minutes, then treated by double ended needle with the solution of the alkynyl zinc chloride prepared above. This mixture was stirred at room temperature for 18 hours, then quenched with ice and 30 ml 3N hydrogen chloride. Product was recovered by extraction with 3×75 ml ether. Ether fractions were combined and washed successively with saturated NaHCO₃ and saturated NaCl solutions and dried (MgSO₄). Solvent was removed in vacuo and the residue purified by flash chromatography (silica; 5% ethyl acetate in hexane) followed by HPLC (Whatman Partisil M-9 10/50; 4% ethyl acetate in hexane) to give the title compound as a colorless oil. PMR (CDCl₃) :δ 1.36 (6H), 1.42 (3H, t, J~7 Hz), 1.93-1.99 (2H, m), 3.03-3.08 (2H, m), 4.40 (2H, q, J~7 Hz), 7.09 (1H, d, J~8.4 Hz), 7.22 (1H, dd, J~8.4 Hz, 2.1 Hz), 7.56 (1H, d, J~2.11 Hz), 7.59 (2H, d, J~7.8 Hz), 8.04 (2H, d, J~7.8 Hz).

Using the same procedure, but substituting the appropriate ethynylthiochroman from Example 4 and the appropriate halo-substituted phenyl ester from Example 5, the following compounds may be prepared:

ethyl 4-[4,4,7-trimethylthiochroman-6-ylethynyl]benzoate;
ethyl 3-[4,4,7-trimethylthiochroman-6-ylethynyl]benzoate;
ethyl 2-[4,4,7-trimethylthiochroman-6-ylethynyl]benzoate;
ethyl 3-[4,4-dimethylthiochroman-6-ylethynyl]benzoate;
ethyl 2-[4,4-dimethylthiochroman-6-ylethynyl]benzoate;
ethyl 4-[4,4-dimethyl-7-ethylthiochroman-6-ylethynyl]benzoate;
ethyl 4-[4,4-dimethyl-7-propylthiochroman-6-ylethynyl]benzoate;
ethyl 4-[4,4-dimethyl-7-hexylthiochroman-6-ylethynyl]benzoate;
ethyl 2-[4-(4,4,7-trimethylthiochroman-6-ylethynyl)phenyl]acetate;
ethyl 2-[4-(4,4-dimethyl-7-ethylthiochroman-6-ylethynyl)phenyl]acetate;
ethyl 2-[4-(4,4-dimethyl-7-propylthiochroman-6-ylethynyl)phenyl]acetate;
ethyl 2-[4-(4,4-dimethyl-7-butylthiochroman-6-ylethynyl)phenyl]acetate;
ethyl 2-[4-(4,4-dimethyl-7-pentylthiochroman-6-ylethynyl)phenyl]acetate;
ethyl 2-[4-(4,4-dimethyl-7-hexylthiochroman-6-ylethynyl)phenyl]acetate;
ethyl 2-[3-(4,4-dimethylthiochroman-6-ylethynyl)phenyl]acetate;
ethyl 2-[2-(4,4-dimethylthiochroman-6-ylethynyl)phenyl]acetate;
ethyl 3-[4-(4,4-dimethylthiochroman-6-ylethynyl) phenyl]propanoate;
ethyl 3-[3-(4,4-dimethylthiochroman-6-ylethynyl)phenyl]propanoate;
ethyl 3-[2-(4,4-dimethylthiochroman-6-ylethynyl)phenyl]propanoate;
ethyl 4-[4-(4,4-dimethylthiochroman-6-ylethynyl)phenyl]butanoate;
ethyl 4-[3-(4,4-dimethylthiochroman-6-ylethynyl)phenyl]butanoate;
ethyl 4-[2-(4,4-dimethylthiochroman-6-ylethynyl)phenyl]butanoate;
ethyl 5-[4-(4,4-dimethylthiochroman-6-ylethynyl)phenyl]pentanoate;
ethyl 5-[3-(4,4-dimethylthiochroman-6-ylethynyl)phenyl]pentanoate;
ethyl 5-[2-(4,4-dimethylthiochroman-6-ylethynyl)phenyl]pentanoate;
ethyl 2-4-(4,4,7-trimethylthiochroman-6-ylethynyl)phenyl]pentanoate;
ethyl 2-[4-(4,4-dimethyl-7-ethylthiochroman-6-ylethynyl)phenyl]pentanoate;
ethyl 2-[4-(4,4-dimethyl-7-propylthiochroman-6-ylethynyl)phenyl]pentanoate;
ethyl 2-[4-(4,4-dimethyl-7-butylthiochroman-6-ylethynyl)phenyl]pentanoate;
ethyl 2-[4-(4,4-dimethyl-7-pentylthiochroman-6-ylethynyl)phenyl]pentanoate; and
ethyl 2-[4-(4,4-dimethyl-7-hexylthiochroman-6-ylethynyl)phenyl]pentanoate.

EXAMPLE 7

Diphenyl-3-methyl-3-buten-1-yl phosphate

To an ice-cooled solution of 12.2 g (141.65 mmol) of 3-methyl-3-buten-1-ol (Aldrich) and 11.9 g (150.44 mmol) of pyridine in 100 ml of tetrahydrofuran was added dropwise under argon a solution of 38.5 g (143.21 mmol) of diphenyl chlorophosphate in 100 ml of tetrahydrofuran. The mixture was heated at reflux for 3 hours and then cooled and filtered. The filtrate was concentrated in vacuo and the residue dissolved in 400 ml of 1:1 ether and hexane and then washed with 2×200 ml water, 75 ml saturated NaCl solution and dried (MgSO₄). The solvent was removed in vacuo to give the title compound as a pale yellow oil. PMR (CDCl): δ 1.69 (3H, s), 2.37 (2H, t, J~7 Hz), 4.32 (2H, q, J~7 Hz), 4.72 (1H, s), 4.80 (1H), 7.10-7.35 (10H, m).

EXAMPLE 8

4,4-Dimethylchroman

To a dry, ice-cooled flask containing 34.95 g (0.134 mol) of stannic chloride was added quickly under argon 63.0 g (0.669 mol) of phenol. The mixture was stirred at 0° C. for 0.5 hour and then treated with 43.0 g (0.135 mol) of diphenyl-3-methyl-3-buten-1-yl phosphate (from Example 7), followed by a 5 ml carbon disulfide rinse. The mixture was stirred at room temperature for 21 hours and then quenched by pouring onto 700 g ice and 1 litre of 1.5N NaOH. The mixture was extracted with 1×600 ml and 2×300 ml ether. The combined ether fractions were washed with 2N NaOH, saturated NaCl and dried (MgSO₄). Solvent was removed in vacuo and the residue purified by flash chromatography (silica; 2% ether in hexane) to give the title compound as a colorless oil. PMR (CDCl₃)67: 1.34 6HCA1°-80-1°85 2HA mCA 4°15-4°20 2HA mcA 6°80 1Ha ddA J~8.1 Hz, 1.5 Hz), (1H, td, J~8.1Hz, 5.1 Hz), 7.07 (1H, td, J~8.1 Hz, 1.5 Hz), 7.26 (1H, dd, J~8.1 Hz, 1.5 Hz).

In a similar manner, but substituting the corresponding 3 alkylphenol for phenol, there may be prepared the following compounds:
4,4,7-trimethylchroman;
4,4-dimethyl-7-ethylchroman;
4,4-dimethyl-7-propylchroman; and
4,4-dimethyl-7-pentylchroman.

EXAMPLE 9

4,4-Dimethyl-6-acetylchroman

To a stirred solution of 7.94 g (48.9425 mmol) of 4,4-dimethylchroman (from Example 8) in 70 ml of nitromethane was added under argon 4.0 g (50.96 mmol) of acetyl chloride followed by 6.8 g (51 mmol) of aluminum chloride. This was stirred at room temperature for 5.5 hours and then cooled in an ice bath and treated slowly with 70 ml of 6N hydrogen chloride. The resultant mixture was stirred at room temperature for 10 minutes and then treated with 100 ml ether and the organic layer separated. The organic layer was washed with water, saturated $NaHCO_3$ and saturated NaCl solutions and dried ($MgSO_4$). Solvent was removed in vacuo and the residue purified by flash chromatography (silica; 10% ethyl acetate in hexanes). This was followed by kugelrohr distillation (95–100° C.; 0.15 mm) to give the title compound as a colorless oil. PMR (CDCl): δ 1.40 (6H), 1.95–2.00 (2H, m), 2.58 (3H), 4.25–4.30 (2H, m), 6.83 (1H, d, J∼8.0 Hz), 7.62 (1H, dd, J∼8.0 Hz, 1.5 Hz), 8.00 (1H, d, J∼1.5 Hz).

Proceeding in the same manner, the other chroman compounds made as per Example 8 are converted to their respective acetyl analogs.

EXAMPLE 10

4.4-Dimethyl-6-ethynylchroman

To a solution of 2.47 g (24.41 mmol) of diisopropylamine in 40 ml dry tetrahydrofuran under argon at −78° C. was added dropwise 15.2 ml of 1.6M (24.32 mmol) n-butyl lithium in hexane. This mixture was stirred at −78° C. for 1 hour and then treated dropwise with a solution of 4.98 g (24.38 mmol) of 4,4-dimethyl-6-acetylchroman (from Example 9) in 4 ml of tetrahydrofuran. After stirring at −78° C. for 1 hour, the solution was treated with 4.2 g (24.36 mmol) of diethyl chlorophosphate. The cooling bath was then removed and the reaction mixture stirred at room temperature for 2.75 hours. This solution was then transferred using a double ended needle to a solution of lithium diisopropyl amide [prepared using 4.95 g (48.92 mmol) of diisopropylamine and 30.5 ml of 1.6M (48.8 mmol) n-butyllithium in hexane] in 80 ml dry tetrahydrofuran at −78° C. The cooling bath was removed and mixture stirred at room temperature for 18 hours and then quenched with 50 ml water and 25 ml of 3N hydrogen chloride. The mixture was extracted with 2×100 ml and 3×50 ml of pentane and the combined organic fractions washed with 3N hydrogen chloride, water, saturated $NaHCO_3$ and saturated NaCl solutions and then dried ($MgSO_4$). Solvent was then removed in vacuo and the residue purified by flash chromatography (silica; 10% ethyl acetate in hexane) followed by kugelrohr distillation (70° C.; 0.35 mm) to give the title compound as a colorless crystalline solid. PMR (CDCl$_3$): δ 1.33 (6H), 1.81–1.86 (2H, m), 3.00 (1H, s), 4.19–4.24 (2H, m), 6.75 (1H, d, J∼8.5 Hz), 7.22 (1H, dd, J∼8.5 Hz, 2.3 Hz), 7.44 (1H, d, J∼2.3 Hz).

Using this method, the acetyl derivatives made in Example 9 are converted to the ethynyl form.

EXAMPLE 11

Ethyl 4-[4,4-dimethylchroman-6-ylethynyl]benzoate

Reaction vessels used in this procedure were flame dried under vacuum and all operations were carried out in an oxygen-free, argon or nitrogen atmosphere. To a solution of 509.4 mg (2.74 mmol) of 4,4-dimethyl-6-ethynyl chroman (from Example 10) in 4 ml of dry tetrahydrofuran at 0° C. was added dropwise 1.72 ml of 1.6M (2.75 mmol) of n-butyl lithium in hexane. Stirring was commenced at 0° C. for 30 minutes and at room temperature for 15 minutes, after which the solution was cooled again to 0° C. and then treated with a solution of 380 mg (2.79 mmol) of fused zinc chloride in 5 ml of dry tetrahydrofuran using a double ended needle. The resulting solution was stirred at 0° C. for 1 hour and then at room temperature for 15 minutes. A solution of 628.6 mg (2.74 mmol) of ethyl 4-bromobenzoate in 4 ml of dry tetrahydrofuran was transferred by double ended needle into a suspension of 380 mg (0.33 mmol) of tetrakistriphenylphosphine palladium in 5 ml dry tetrahydrofuran and stirred at room temperature for 15 minutes, then treated by double ended needle with the solution of alkynyl zinc chloride prepared above. The mixture was stirred at room temperature for 20 hours and then quenched with ice and 30 ml of 3N hydrogen chloride. The mixture was then extracted with 3×75 ml ether and ether extracts were combined and washed successively with saturated $NaHCO_3$ and saturated NaCl solutions and then dried ($MgSO_4$). Solvent was removed in vacuo and the residue further purified by flash chromatography (silica; 10% ethyl acetate in hexane) to obtain the captioned compound as a white solid. PMR (CDCl$_3$): δ 1.36 (6H), 1.42 (3H, t, J∼7.3 Hz), 1.82–1.86 (2H, m), 4.21–4.25 (2H, m), 4.40 (2H, q, J∼7.3 Hz), 6.79 (1H, d, J∼8.1 Hz), 7.28 (1H, dd, J∼8.1 Hz, 2.2 Hz), 7.50 (1H, d, J∼2.2 Hz), 7.58 (2H, d, J∼8.7 Hz), 8.03 (2H, d, J∼8.7 Hz).

Using the same procedure, but substituting an appropriate ethynylchroman from Example 10 and the appropriate halo-substituted phenyl ester from Example 5, the following exemplary compounds can be prepared.
ethyl 4-[4,4,7-trimethylchroman-6-ylethynyl]benzoate;
ethyl 4-[4,4-dimethyl-7-ethylchroman-6-ylethynyl]benzoate;
ethyl 4-[4,4-dimethyl-7-propylchroman-6-ylethynyl]benzoate;
ethyl 4-[4,4-dimethyl-7-hexylchroman-6-ylethynyl]benzoate;
ethyl 3-[4,4,7-trimethylchroman-6-ylethynyl]benzoate;
ethyl 2-[4,4,7-trimethylchroman-6-ylethynyl]benzoate;
ethyl 3-[4,4-dimethylchroman-6-ylethynyl]benzoate;
ethyl 2-[4,4-dimethylchroman-6-ylethynyl]benzoate;
ethyl 2-[4-(4,4,7-trimethylchroman-6-ylethynyl)phenyl]acetate;
ethyl 2-[4-(4,4-dimethyl-7-ethylchroman-6-yl]ethynyl)phenyl]acetate;
ethyl 2-[4-(4,4-dimethyl-7-propylchroman-6-yl]ethynyl)phenyl]acetate;
ethyl 2-[4-(4,4-dimethyl-7-butylchroman-6-yl]ethynyl)phenyl]acetate;
ethyl 2-[4-(4,4-dimethyl-7-pentylchroman-6-yl]ethynyl)phenyl]acetate;
ethyl 2-[4-(4,4-dimethyl-7-hexylchroman-6-yl]ethynyl)phenyl]acetate;

ethyl 2-[3-(4,4-dimethylchroman-6-ylethynyl]phenyl]acetate;

ethyl 2-(2-(4,4-dimethylchroman-6-ylethynyl]phenyl]acetate;

ethyl 3-[4-(4,4-dimethylchroman-6-ylethynyl]phenyl]propanoate;

ethyl 3-[3-(4,4-dimethylchroman-6-ylethynyl]phenyl]propanoate;

ethyl 3-(2-(4,4-dimethylchroman-6-ylethynyl]phenyl]propanoate;

ethyl 4-[4-(4,4-dimethylchroman-6-ylethynyl]phenyl]butanoate;

ethyl 4-[3-(4,4-dimethylchroman-6-ylethynyl]phenyl]butanoate;

ethyl 4-[2-(4,4-dimethylchroman-6-ylethynyl]phenyl]butanoate;

ethyl 5-[4-(4,4-dimethylchroman-6-ylethynyl]phenyl]pentanoate;

ethyl 5-[3-(4,4-dimethylchroman-6-ylethynyl]phenyl]pentanoate;

ethyl 5-[2-(4,4-dimethylchroman-6-ylethynyl]phenyl]pentanoate;

ethyl 2-[4-(4,4,7-trimethylchroman-6-ylethynyl]phenyl]pentanoate;

ethyl 2-[4-(4,4-dimethyl-7-ethylchroman-6-yl)ethynyl)phenyl]pentanoate;

ethyl 2-[4-(4,4-dimethyl-7-propylchroman-6-yl)ethynyl)phenyl]pentanoate;

ethyl 2-[4-(4,4-dimethyl-7-butylchroman-6-yl)ethynyl)phenyl]pentanoate;

ethyl 2-[4-(4,4-dimethyl-7-pentylchroman-6-yl)ethynyl)phenyl]pentanoate; and ethyl 2-[4-(4,4-dimethyl-7-hexylchroman-6-yl)ethynyl)phenyl]pentanoate.

EXAMPLE 12

4-[4,4-dimethylchroman-6-ylethynyl]benzoic acid and 4-[4,4-dimethylthiochroman-6-ylethynyl]benzoic acid The absolute ethanol used in this experiment was degassed by applying a vacuum while simultaneously bubbling nitrogen through it. A solution of 101.1 mg (0.30 mmol) of ethyl 4-[(4,4-dimethylchroman-6-yl)ethynyl]benzoate (from Example 11) in 2 ml ethanol was treated under argon with 0.7 ml of a 1.81M (1.27 mmol) solution of potassium hydroxide in ethanol and water. This mixture was stirred at room temperature for 60 hours and then solvent was removed in vacuo. The residue was dissolved in 25 ml of water and extracted with 25 ml of ether and the ether extract discarded. The aqueous layer was acidified with glacial acetic acid and extracted with 4×50 ml of ether. Ether extracts were combined and washed with water, then saturated NaCl solution and dried (MgSO4). Solvent was then removed in vacuo to give the title compound as a white solid. PMR ((CD3)2CO): δ 1.39 (6H), 1.86–1.90 (2H, m), 4.23–4.27 (2H, m), 6.79 (1H, d, J~8.4 Hz), 7.28 (1H, dd, J~8.4 Hz, 1.9 Hz), 7.50 (1H, d, J~1.9 Hz), 7.61 (2H, d, J~8.3 Hz), 8.08 (2H, d, J~8.3 Hz).

Employing the general procedure described above but using instead ethyl 4-[4,4-dimethylthiochroman-6-ylethynyl]benzoate (from Example 6), 4-[4,4-dimethylthiochroman-6-ylethynyl]benzoic acid was synthesized as a white solid. PMR ((CD3)2CO): δ 1.34(6H), 1.93–1.98 (2H, m), 3.06–3.10 (2H, m), 7.09 (1H, d, J~8.5 Hz), 7.23 (1H, dd, J~8.5 Hz, 1.7 Hz), 7.62 (1H, d, J~1.7 Hz), 7.63 (2H, d, J~9.0 Hz), 8.03 (2H, d, J~9.0 Hz).

Proceeding in a similar manner, esters of this invention may be converted to their corresponding acids.

EXAMPLE 13

4-[4,4-dimethylchroman-6-ylethynyl]benzyl alcohol

A 250 ml 3-necked flask is fitted with a stirrer, a dripping funnel, a nitrogen inlet and a thermometer. In the flask is placed a solution of 379.5 mg (10 mmol) of lithium aluminum hydride in 30 ml of dry diethyl ether. The solution is cooled to −65° C. under nitrogen and a solution of 3.3441 g (10 mmol) of ethyl-4-((4,4-dimethylchroman-6-ylethynyl)benzoate in 15 ml of dry ether is added dropwise at a rate such that the temperature does not exceed -60° C. The mixture is stirred at −30° C. for 1 hour and the excess hydride is then destroyed by the addition of 300 mg (3.4 mmol) of ethyl acetate. The reaction mixture is then hydrolyzed by adding 3 ml of saturated ammonium chloride solution and allowing the temperature to rise to room temperature. The mixture is then filtered and the residue washed with ether. The ether layer is then washed with saturated sodium chloride solution, dried (MgSO4) and then concentrated in vacuo. The residue is purified by chromatography followed by recrystallization to give the title compound.

By the same process, the esters or acids of this invention may be converted to their corresponding primary alcohol analog.

EXAMPLE 14

4-[4,4-dimethylchroman-6-ylethynyl]-1-acetoxymethylbenzene

A solution of 2.92 g (10 mmol) of 4-[(4,4-dimethylchroman-6-ylethynyl]benzyl alcohol, 600 mg (10 glacial acetic acid, 2.06 g (10 mmol) of dicyclohexylcarbodiimide and 460 mg (3.765 mmol) of 4-dimethylaminopyridine in 150 ml methylene chloride is stirred at room temperature for 48 hours. The reaction mixture is then filtered and the residue washed with 50 ml of methylene chloride. The filtrate is then concentrated in vacuo and the residue is purified by chromatography followed by recrystallization to give the title compound.

This procedure may be used to esterify any of the primary alcohols of this invention.

EXAMPLE 15

4-[4,4-dimethylchroman-6-ylethynyl]-benzaldehyde

A solution of 1.396 g (11 mmol) of freshly distilled oxalyl chloride in 25 ml of methylene chloride is placed in a 4-necked flask equipped with a stirrer, a thermometer and two pressure-equalizing addition funnels fitted with drying tubes. The solution is cooled to −60° C. and then treated dropwise with a solution of 1.875 g (24 mmol) of dimethyl sulfoxide (distilled from calcium hydride) in 5 ml of methylene chloride over a five minute period. The reaction mixture is then stirred at −60° C. for an additional 10 minutes. A solution of 2.92 g (10 mmol) of 4-[(4,4-dimethylchroman-6-ylethynyl]benzyl alcohol in 10 ml of methylene chloride is then added to the reaction mixture over a period of 5 minutes. The mixture is stirred for a further 15 minutes and is then treated with 5.06 g (50 mmol) of triethylamine. The cooling bath is then removed and the mixture is allowed to warm to room temperature. Thirty ml of water is then added to the mixture and stirring is continued for a further 10 mintues. The organic layer is then separated and the aqueous layer is extracted with 20 ml of methylene chloride. The organic layers are then combined and washed successively with dilute HCl, water and dilute Na₂CO₃ solution and then dried (MgSO₄). The solution is then filtered and concentrated in vacuo and the residue is purified by chromatography followed by recrystallization to give the title compound.

The alcohols of this invention may be oxidized to their corresponding aldehyde or ketone by this method.

EXAMPLE 16

4-[4,4-Dimethylchroman-6-ylethynyl]-1-(1-hydroxypropyl)benzene

Four ml of a 3M (12 mmol) solution of ethyl magnesium bromide in ether is placed in a 3-necked flask fitted with a mechanical stirrer, a reflux condenser protected by a drying tube and a pressure-equalizing dropping funnel protected by a drying tube. The flask is cooled in an ice-bath and a solution of 2.9 g (10 mmol) of the carboxaldehyde from Example 15 in 10 ml of dry ether is added slowly with vigorous stirring. The cooling bath is then removed and the mixture heated at reflux for 3 hours. The mixture is then cooled in an ice-salt bath and 5 ml of saturated ammonium chloride solution is added. The mixture is stirred for a further 1 hour and then filtered and the residue washed with two 10 ml portions of ether. The ether solution is then separated, dried (MgSO₄) and the ether removed in vacuo. The residue is then purified by chromatography followed by recrystallization to give the title compound.

Using the same procedure, but substituting another aldehyde, any of the other aldehydes of this invention can be converted to a secondary alcohol.

EXAMPLE 17

4-[4,4-Dimethylchroman-6-ylethynyl]-1-dimethoxymethylbenzene

A round-bottomed flask is fitted with a Dean-Stark apparatus under a reflux condenser protected by a drying tube. A mixture of 3.48 g (12 mmol) of 4-[(4,4-dimethylchroman-6-ylethynyl]benzaldehyde, 4.80 mg (15 mmol) of anhydrous methanol, 2 mg of p-toluenesulfonic acid monohydrate and 10 ml of anhydrous benzene is placed in the flask and the mixture heated at reflux under nitrogen until close to the theoretical amount of water is collected in the Dean-Stark trap. The reaction mixture is cooled to room temperature and extracted successively with 5 ml of 10% sodium hydroxide solution and two 5 ml portions of water and then dried (MgSO₄). The solution is then filtered and the solvent removed in vacuo. The residue is purified by chromatography and then recrystalliztion to give the title compound.

In a similar manner, any aldehyde or ketone of this invention may be converted to an acetal or a ketal.

EXAMPLE 18

Preferably, these compounds may be administered topically using various formulations. Such formulation may be as follows.

| Ingredient | Weight/Percent |
| --- | --- |
| Solution | |
| Retinoid | 0.1 |
| BHT | 0.1 |
| Alcohol USP | 58.0 |
| Polyethylene Glycol 400 NF | 41.8 |

| Ingredient | Weight/Percent |
| --- | --- |
| Gel | |
| Retinoid | 0.1 |
| BHT | 0.1 |
| Alcohol USP | 97.8 |
| Hydroxypropyl Cellulose | 2.0 |

What is claimed is:

1. A compound of the formula

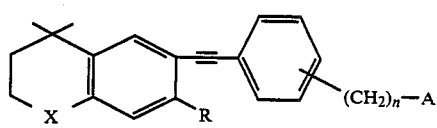

where X is S, O or $NR_1$ where $R_1$ is hydrogen or lower alkyl; n is 0-5; R is H or lower alkyl and A is H, —COOH or a pharmaceutically acceptable salt, ester of saturated aliphatic alcohols of ten or fewer carbon atoms, or the cyclic or saturated aliphatic cyclic alcohols of 5 to 10 carbon atoms, phenol, or amide or mono- or di-substituted amide of saturated aliphatic alcohols of ten or fewer carbon atoms, or the cyclic or saturated aliphatic cyclic radicals of 5 to 10 carbon atoms thereof, —CH₂OH or a lower alkyl ether or ester of saturated aliphatic acids of ten or fewer carbon atoms or the cyclic or saturated aliphatic cyclic acids of 5 to 10 carbon atoms, and benzoic acid derivative thereof, or —CHO or a lower alkyl acetal derivative thereof, or —COR₂ or a lower alkyl ketal derivative thereof where $R_2$ is —(CH₂)$_m$CH₃ where m is 0-4; or a pharmaceutically acceptable salt.

2. A compound of claim 1 where X is S and n is 0, 1 or 2.

3. A compound of claim 2 where A is —COOH or a pharmaceutically acceptable salt, ester or amide thereof.

4. A compound of claim 3 which is 4-[4,4-dimethylthiochroman-6-ylethynyl]benzoic acid or a pharmaceutically accpetable salt.

5. A compound of claim 3 which is ethyl 4-[4,4-dimethylthiochroman-6-ylethynyl]benzoate.

6. A compound of claim 2 where A is hydrogen.

7. A compound of claim 2 where A is —CH₂OH or an ether or ester derivative thereof.

8. A compound of claim 2 where A is —CHO or an acetal derivative thereof.

9. A compound of claim 2 where A is —COR₂ or a ketal derivative thereof where $R_2$ is —(CH₂)$_m$CH₃ where m is 0-4.

10. A compound of claim 1 where X is O and n is 0, 1 or 2.

11. A compound of claim 10 where A is —COOH or a pharmaceutically acceptable salt, ester or amide thereof.

12. A compound of claim 11 which is ethyl 4-[4,4-dimethylchroman-6-ylethynyl]benzoate.

13. A compound of claim 11 which is 4-[4,4-dimethylchroman-6-ylethynyl]benzoic acid or a pharmaceutically acceptable salt thereof.

14. A compound of claim 10 where A is hydrogen.

15. A compound of claim 10 where A is —CH₂OH or an ether or ester derivative thereof.

16. A compound of claim 10 where A is —CHO or an acetal derivative thereof.

17. A compound of claim 10 where A is —COR$_2$ or a ketal derivative thereof where R$_2$ is -(CH$_2$)$_m$CH$_3$ where m is 0–4.

18. A pharmaceutical composition comprising a thrapeutically effective amount of a compound of formula I and pharmaceutically acceptable excipient wherein formula I is

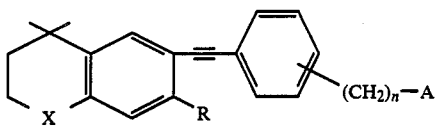

where X is S, O or NR$_1$ where R$_1$ is hydrogen or lower alkyl; n is 0–5; R is H or lower alkyl and A is H, —COOH or a pharmaceutically acceptable salt, ester of saturated aliphatic alcohols of ten or fewer carbon atoms, or the cyclic or saturated aliphatic cyclic alcohols of 5 to 10 carbon atoms, phenol, or amide or mono- or di-substituted amide of saturated aliphatic alcohols of ten or fewer carbon atoms, or the cylic or saturated aliphatic cyclic radicals of 5 to 10 carbon atoms thereof, —CH$_2$OH or a lower alkyl ether or esther of saturated aliphatic acids of ten or fewer carbon atons or the cyclic or saturated aliphatic cyclic acids of 5 to 10 carbon atoms, and benzoic acid derivative thereof, or —CHO or a lower alkyl acetal derivative thereof, or —COR$_2$ or a lower akyl ketal derivative thereof where R$_2$ is —(CH$_2$)$_m$CH$_3$ where m is 0–4; or a pharmaceutically acceptable salt.

19. A composition according to claim 14 having antipsoriatic activity in a mammal.

20. A method for treating psoriasis in a mammal which method comprises administering alone or in conjunction with a pharmaceutically acceptable excipient, a therapeutically effective amount of a compound of the formula

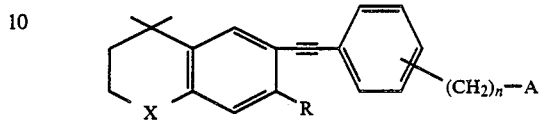

or lower where X is S, O or NR$_1$ where R$_1$ is hydrogen alkyl; n is 0–5; R is H or lower alkyl and A is H, —COOH or a pharmaceutically acceptable salt, ester of saturated aliphatic alcohhols of ten or fewer carbon atoms, or the cyclic or saturated aliphatic cyclic alcohols of 5 to 10 carbon atoms, phenol, or amide or mono- or di-substituted amide of saturated aliphatic alcohols of ten or fewer carbon atoms, or the cyclic or saturated aliphatic cylic radicals of 5 to 10 carbon atoms thereof, —CH$_2$OH or a lower alkyl ether or ester of saturated aliphatic acids of ten or fewer carbon atons or the cyclic or saturated aliphatic cyclic acids of 5 to 10 carbon atoms, and benzoic acid derivative thereof, or —CHO or a lower alkyl acetal derivative thereof, or —COR$_2$ or a lower alkyl ketal derivative thereof where R$_2$ is —(CH$_2$)$_m$CH$_3$ where m is 0–4; or a pharmaceutically acceptable salt.

* * * * *